US005762805A

United States Patent [19]
Truitt et al.

[11] Patent Number: 5,762,805
[45] Date of Patent: Jun. 9, 1998

[54] TECHNIQUE FOR EXTRACORPOREAL TREATMENT OF BLOOD

[75] Inventors: Lori A. Truitt, Golden; Frank Corbin, III, Littleton, both of Colo.; Donn D. Lobdell, Corona Del Mar, Calif.; Douglas P. Miller, Broomfield, Colo.; Keith Manica, Lakewood, Colo.; George J. Eilers, Evergreen, Colo.; Steven H. Johnson, Lakewood, Colo.; Lawrence L. Leppert, Littleton, Colo.

[73] Assignee: COBE Laboratories, Inc., Lakewood, Colo.

[21] Appl. No.: 480,489

[22] Filed: Jun. 7, 1995

Related U.S. Application Data

[63] Continuation of Ser. No. 17,571, Feb. 12, 1993.
[51] Int. Cl.⁶ .............. B01D 61/00; B01D 61/32; A61M 1/14
[52] U.S. Cl. .............. 210/645; 210/646; 210/739; 210/929; 604/4
[58] Field of Search .............. 210/85, 90, 96.1, 210/97, 101, 134, 138, 143, 195.2, 257.1, 257.2, 258, 259, 321.71, 416.1, 433.1, 645, 646, 739, 649, 805, 929; 604/4, 5, 6, 65, 66, 67; 422/48; 177/45, 50; 364/184, 185, 188, 189, 413.01, 413.02, 413.07, 550, 552, 579, 567, 580, 581

[56] References Cited

U.S. PATENT DOCUMENTS

| | | | |
|---|---|---|---|
| 4,132,644 | 1/1979 | Kolberg | 210/85 |
| 4,178,240 | 12/1979 | Pinkerton | 417/404 |
| 4,204,957 | 5/1980 | Weickhardt | 210/98 |

(List continued on next page.)

FOREIGN PATENT DOCUMENTS

| | | |
|---|---|---|
| 0228160 | 9/1982 | European Pat. Off. |
| 0189561 | 12/1985 | European Pat. Off. |
| 0192588 | 8/1986 | European Pat. Off. |
| 0321754 | 6/1989 | European Pat. Off. |
| 0373455 | 6/1990 | European Pat. Off. |
| 2390173 | 12/1978 | France |
| 2397197 | 2/1979 | France |
| 2703188 | 8/1978 | Germany |
| WO 85/03879 | 10/1991 | WIPO |
| WO 91/15253 | 10/1991 | WIPO |

OTHER PUBLICATIONS

J.V. Leins, M.D., et al., "Arteriovenous Hemofiltration with Dialysis", Critical Care Report 1990, pp. 408–414.
"Buffer Balance in Bicarbonate Hemofiltration", American Society for Artificial Internal Organs 32, Jul.–Sep. 1986, No. 1, Hagerstown, MD, USA, pp. 422–424.

(List continued on next page.)

Primary Examiner—John Kim
Attorney, Agent, or Firm—Carol W. Burton, Esq.; Holland & Hart LLP

[57] ABSTRACT

Blood from a patient is treated extracorporeally by any selected one of a plurality of predetermined treatments. Each of the treatments involves the flow of blood from the patient into a primary chamber of a filtration unit, past a semipermeable membrane located in the filtration unit which separates the primary chamber from a secondary chamber of the filtration unit, out the filtration unit and back to the patient. A replacement fluid is selectively and controllably added to the blood, as required for the selected treatment. A secondary fluid is controllably and selectively introduced into the secondary chamber of the filtration unit for controllably collecting material passing across the semipermeable membrane from the blood or for supplying material to pass across the semipermeable membrane into the blood as required for the selected treatment. Materials are removed from the secondary chamber and collected in accordance with the selected treatment. Blood leaks into the secondary chamber are automatically detected and the rates of blood and fluid flow automatically adjusted in response thereto. An apparatus which automatically performs and monitors the selected treatment is also described.

4 Claims, 5 Drawing Sheets

U.S. PATENT DOCUMENTS

| | | | |
|---|---|---|---|
| 4,324,663 | 4/1982 | Hirel et al. | 210/646 |
| 4,372,846 | 2/1983 | Yamagami | 210/929 |
| 4,379,452 | 4/1983 | DeVries | 604/6 |
| 4,526,515 | 7/1985 | DeVries | 604/6 |
| 4,582,598 | 4/1986 | Bilstad et al. | 210/101 |
| 4,600,401 | 7/1986 | Kamen | 604/65 |
| 4,606,826 | 8/1986 | Sano et al. | 210/929 |
| 4,684,460 | 8/1987 | Issautier | 210/90 |
| 4,708,802 | 11/1987 | Rath et al. | 210/651 |
| 4,711,715 | 12/1987 | Polaschegg | 210/103 |
| 4,728,433 | 3/1988 | Buck et al. | 210/646 |
| 4,767,399 | 8/1988 | Bollish | 604/5 |
| 4,769,132 | 9/1988 | Patono | 210/95 |
| 4,844,810 | 7/1989 | Richalley et al. | 210/646 |
| 4,889,635 | 12/1989 | Chevallet | 210/321.71 |
| 4,923,598 | 5/1990 | Schäl | 210/87 |
| 4,980,054 | 12/1990 | Lavender | 210/90 |
| 5,211,849 | 5/1993 | Kitaevich et al. | 210/645 |
| 5,326,476 | 7/1994 | Grogan et al. | 210/646 |

OTHER PUBLICATIONS

"Sartorius Hemoprocessor® 400 20", Operating Instructions, Sartorius GmbH, Gottingen, Germany, (1984).

Gambro®, "Operator's Manual for Hemofiltration BMM 10–1 and HFM 10–1", AK–10 System for Hemofiltration, GambroAB, Lund Sweden. (1986).R.L. Menta, "New Developments in Continous Arteriovenous Hemofiltration/Dialysis", International Yearbook of Nephrology 1992, pp. 271–295.

Renal Intensive Care Program, Hospal Ltd., Basel, Switzerland. (undated).

"MONITRAL®S Biofiltration Acetate Free" and MONITRAL®SC Biofiltration Acetate Free, Hospal publ. in or before Jan. 1993, Meyzieu Cedex, France.

"COBE Centrysystem™ 3 Dialysis Control Unit—Operator's Manual", COBE Laboratories, Inc. Sep. 1988, Lakewood, Colorado.

"International Standard—Medical Electrical Equipment Part 2: Particular requirements for safety of haemodialysis equipment", IEC, pp. 31 and 35, 1989, Brussels, Belgium.

"Hemofilter and Hemoprocessor—A New System for Hemofiltration", Sartorius–Membranfilter GmbH, publ. on or before Jan. 29, 1993, Göttingen, Germany.

"Instruction Manual BSM 22SC", Rev. A, pp. 29, 30 and 57, Hospal Mar. 1990, Meyzieu Cedex, France.

J.H. Holmes et al., "Removal of Fluid From the Patient During Hemodialysis", Dept. of Medicine, Univ. of Colorado, 1969.

"International Standard CEI IEC 601–2–16", ©1989 Bureau International Electrotechnical Commission, Geneva, Switzerland.

"Centrysystem™ 3—Precise Ultrafiltration Control", ©1987 COBE Laboratories, Inc. Lakewood, Colorado.

"Hemofiltration in Perspective", 1988 Gambro Ltd., Sidcup, United Kingdom.

C. Ronco et al., "Technical and Clinical Evaluation of a New System for Ultrafiltration Control During Hemodialsis", 1988 Tran. Amer. Society Artif. Intern. Organs, pp. 613–616.

Fig_1

Fig-2

Fig_3a

Fig._3b

Fig_4

TECHNIQUE FOR EXTRACORPOREAL TREATMENT OF BLOOD

RELATED APPLICATIONS

This application is a continuation application of copending U.S. patent application Ser. No. 08/017,571 FOR TECHNIQUE FOR EXTRACORPOREAL TREATMENT OF BLOOD, filed Feb. 12, 1993, which application is related to U.S. patent application Ser. No. 07/942,466, filed concurrently therewith, for Integrated Blood Treatment Fluid Module, which is assigned to the assignee hereof. The disclosure of this related application is incorporated herein by this reference.

This invention relates to extracorporeal treatment of blood, and more particularly, to a new and improved apparatus and methodology for extracorporeal treatment of blood in which any of a plurality of treatments may be selected and automatically performed.

BACKGROUND OF THE INVENTION

Extracorporeal blood treatment involves removing blood from a patient, treating the blood externally to the patient, and returning the treated blood to the patient. Extracorporeal blood treatment is typically used to extract undesirable matter or molecules from the patient's blood and/or add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood to maintain an acid/base balance or to remove excess body fluids, for example.

Extracorporeal blood treatment is typically accomplished by removing the blood from the patient in a continuous flow, introducing the blood into a primary chamber of a filtration unit where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In ultrafiltration (UF) treatment, undesirable matter is removed from the blood by convection across the membrane into the secondary chamber. In a hemofiltration (HF) treatment, the blood flows past the semipermeable membrane as in UF and desirable matter is added to the blood, typically by dispensing a fluid into the treated blood either before or after it passes through the filtration unit and before it is returned to the patient. In a hemodialysis (HD) treatment, a secondary fluid containing desirable matter is introduced into the secondary chamber of the filtration unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF. To perform one of these extracorporeal blood treatments, blood must be continuously removed from either a vein or artery of the patient.

Traditionally each type of extracorporeal blood treatment has been conducted with a separate system because of the unique combination of fluids, flow rates, pressures and other parameters associated with each of the treatments. So, for example, manual systems used to perform HD on arterial blood rely on the arterial blood pressure to cause blood to flow past the membrane and be treated. Because a natural flow cannot be achieved when using venous blood, these systems cannot perform HD on venous blood and a separate machine or pump is required to establish a blood flow from a venous blood source and cause the venous blood to pass through the filtration unit and return the treated blood to a venous return point.

Traditionally, setup, monitoring and adjusting of each separate system or machine has been labor intensive. Setup, which includes assembling and priming of the extracorporeal blood treatment apparatus, can be especially time consuming. These manual systems are further labor intensive because of the need for personnel often to monitor continuously and to adjust fluid flow rates based upon visual observation. For example, during operation of some extracorporeal blood treatment machines, operators can only adjust the rate of removal of body fluid from the secondary chamber by raising or lowering the height of a container collecting the matter from the secondary chamber. Changing the height of the collection container effectively modifies the pressure across the semipermeable membrane, increasing or decreasing the rate at which body fluid passes from the blood across the membrane. To maintain the rates, the height of the collection container requires continual monitoring so that required adjustments may be made.

The connection of some manual extracorporeal treatment systems to patients can also be labor intensive, with connection to an artery of the patient particularly problematical. An arterial catheter connection must be constantly monitored, as it is susceptible to disconnection and any such disconnection can result in significant blood loss.

Previous extracorporeal blood treatment systems frequently require an operator to constantly monitor the treatment to detect operational conditions placing the patient at risk. Such conditions include leaking of blood at connection points of the blood flow lines to and from the extracorporeal blood treatment machine, clotting of blood in the semipermeable membrane, depletion of fluids in the containers of matter required for treatment, filling of the containers collecting matter during treatment, and existence of dangerously high or low pressures of blood or fluids during the treatment.

It is against this background that the significant improvements and advancements of the present invention have taken place in the field of extracorporeal treatment of blood.

SUMMARY OF THE INVENTION

A significant object of the present invention relates to extracorporeal blood treatment with a single apparatus which is capable of a plurality of extracorporeal blood treatments. A further object of the present invention is the performance of an extracorporeal blood treatment by automatically calculating, performing and monitoring the extracorporeal blood treatment based upon a choice of at treatment by the operator. Another object is to automatically ascertain treatment conditions which place the patient at risk and to automatically correct such conditions and/or notify the operator about such conditions during the extracorporeal treatment of blood. Another object is to notify the operator of conditions requiring operator assistance.

In accordance with these and other objects, the present invention relates to treating blood from a patient extracorporeally by any selected one of a plurality of predetermined treatments. Each of the treatments transfers matter to or from the blood across a semipermeable membrane which is part of a filtration unit having a primary chamber and a secondary chamber which are separated by the semipermeable membrane. The primary chamber receives the blood from the patient and the matter diffused across the semipermeable membrane into the blood and the secondary chamber receives the matter and, possibly, body fluid transferred by diffusion or convection across the semipermeable membrane from the blood. The primary chamber is part of a primary flow circuit which establishes an extracorporeal blood flow from the patient through the primary chamber and back to the patient. Replacement fluid may be added to the blood in the extracorporeal circuit prior to returning the blood to the patient. A secondary flow circuit is connected to the secondary chamber to introduce a secondary fluid into the secondary chamber and to remove fluid collected from the secondary chamber. In accordance with any one of the plurality of treatments selected to be performed, the rate of flow of blood through the primary circuit, the rate of adding replacement fluid to the blood and the rate of introducing secondary fluid into the secondary chamber are selected and the rate of collection fluid from the secondary chamber is calculated. Blood is automatically caused to flow though the primary circuit, replacement fluid is automatically added to the blood in the primary circuit, secondary fluid is automatically introduced into the secondary chamber and fluid is automatically collected from the secondary chamber, in accordance with the selected treatment protocol. A blood leak detector detects blood leaking into the secondary circuit, and automatically puts the apparatus in a safe state in response thereto. The blood leak detector automatically performs self-tests to determine the operational integrity thereof.

These and other features of the present invention can be better understood from the following detailed description of a preferred embodiment of the present invention, taken in conjunction with the accompanying drawings that are briefly described below.

DETAILED DESCRIPTION

Figure 1:
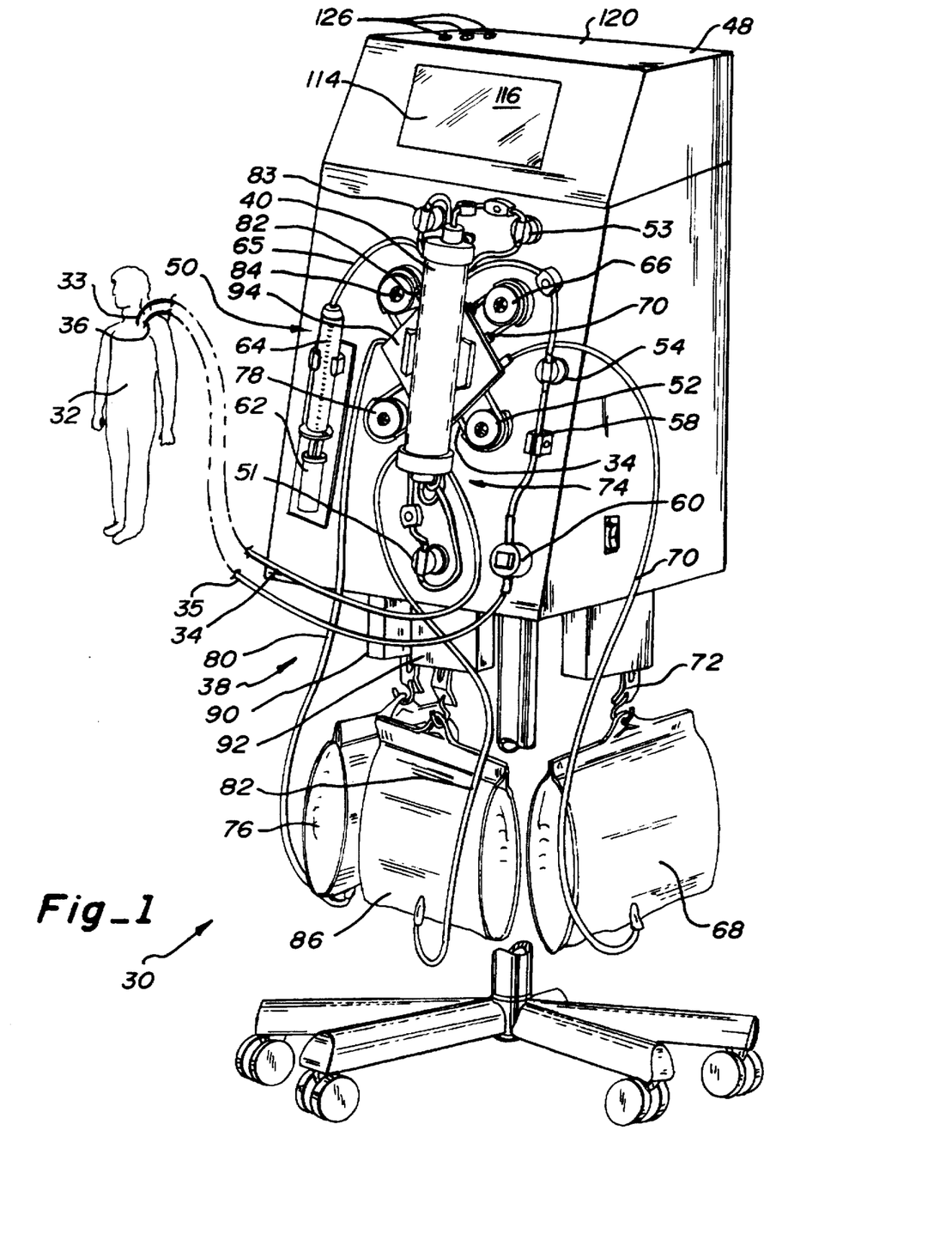
FIG. 1 is an illustration of an extracorporeal blood treatment apparatus incorporating the present invention, attached to a patient undergoing extracorporeal blood treatment.
Figure 2:
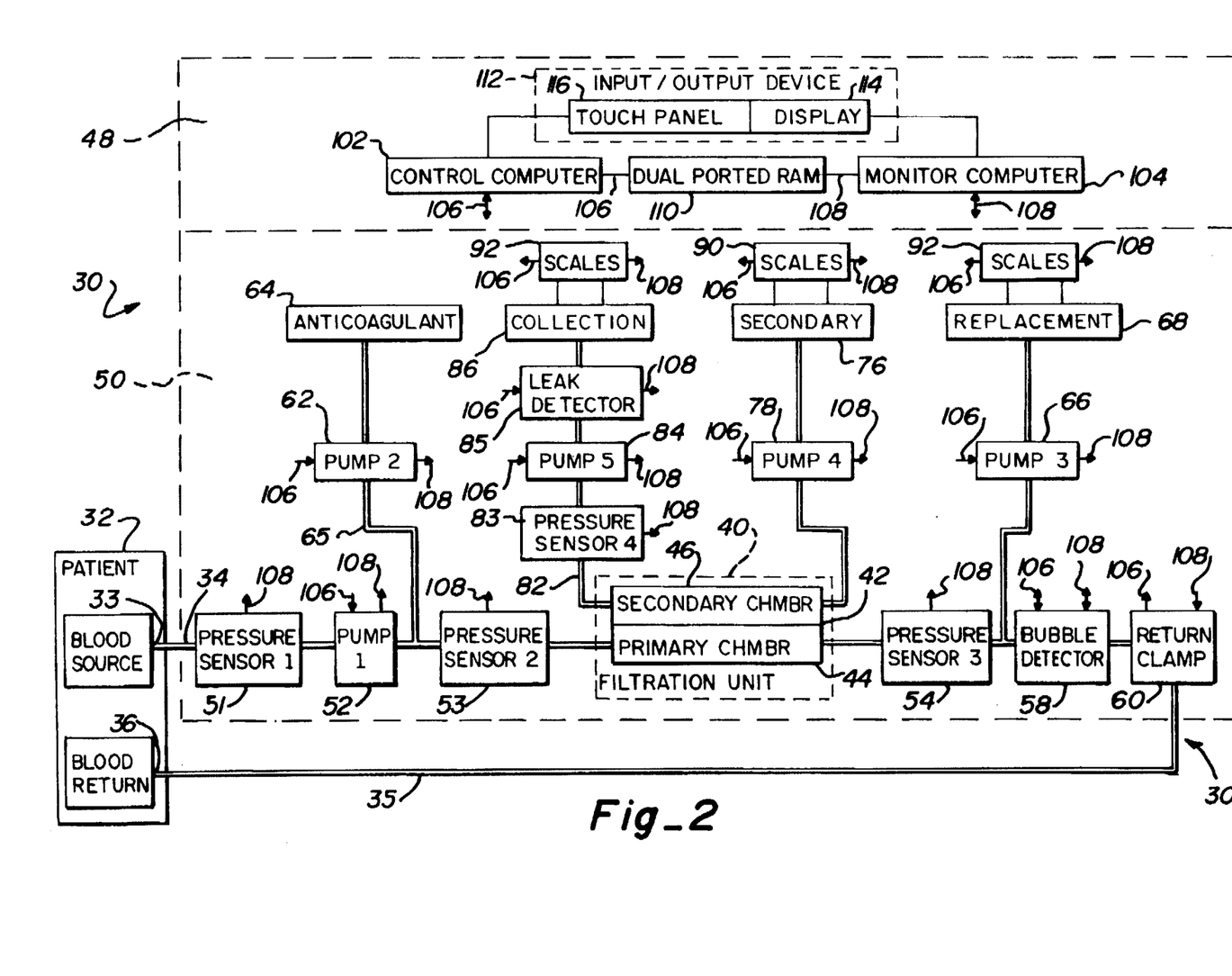
FIG. 2 is a block diagram of the two parts of the extracorporeal blood treatment apparatus shown in FIG. 1.

The presently preferred embodiment of an apparatus 30 for treating extracorporeally blood from a patient 32 is illustrated in FIGS. 1 and 2. Blood is removed from the patient 32 through a catheter 33 inserted into a vein or artery of the patient and flows into an access line 34 for supply to the apparatus 30. The apparatus 30 processes the blood for each of a number of extracorporeal blood treatment protocols and returns the processed or treated blood to the patient though a return line 35 and a return catheter 36 inserted into a vein of the patient. The blood flow path from the patient 32 which includes the catheter 33, the access line 34 to the apparatus 30, and the return line 35 and return stick 36 back to the patient forms a primary blood flow circuit 38.

Each of the treatment protocols involves passing the blood in the primary circuit 38 through a filtration unit 40. The filtration unit 40 uses a conventional semipermeable membrane 42 (FIG. 2) which divides the filtration unit 40 into a primary chamber 44 and a secondary chamber 46. The semipermeable membrane 42 confines the blood in the primary circuit 38 to the primary chamber 44. The semipermeable membrane 42 allows matter or molecules from the blood in the primary chamber 44 to migrate (by diffusion or convection) across the semipermeable membrane into the secondary chamber 46, and possibly allow matter or molecules from the secondary chamber to diffuse across the semipermeable membrane into the blood in the primary chamber. In all cases, each treatment protocol involves removing extracorporeally undesired matter from the blood or adding extracorporeally desirable matter to the blood.

To select, control and monitor each of the treatment protocols, the apparatus 30 includes a protocol selection, control and monitoring system 48 which is generally shown in FIG. 2. The selection, control and monitoring (SCM) system 48 interacts with the remaining components of the apparatus 30 which are generally shown in FIG. 1 and in block diagram form at 50 in FIG. 2.

One of the components 50 is a first pressure sensor 51 connected in the access line 34. The first pressure sensor 51 allows the blood pressure of the access line 34 to be monitored, among other things.

A first pump 52 is connected in the access line 34 and controls the rate of blood flow through the primary circuit 38. Typically, the first pump 52 is operated when the blood to be treated is withdrawn from a vein of the patient 32 through a venous catheter 33. The first pump 52 creates a pressure in the return line 34 which is higher than the blood pressure in the return vein in which the return catheter 36 is inserted. The pressure differential created by the first pump 52 forces blood from the venous blood source through the catheter 33, through the primary circuit 38 and through the return catheter 36 into the lower pressure environment of the return vein of the patient.

A second pressure sensor 53 is connected in the primary circuit 38 between the first pump 52 and an entrance to the primary chamber 44. One function of the second pressure sensor 53 is to detect and monitor the pressure of the blood supplied to an entrance to the primary chamber 44. An alarm condition is indicated, for example, if the blood pressure at the entrance falls below a predetermined value, in which case blood may be leaking.

A third pressure sensor 54 is connected at the outlet of the primary chamber 44. One of functions of the third pressure sensor 54 is to monitor the pressure of the blood in the return line 35 at the exit from the primary chamber 44. By comparing the pressures sensed by the sensors 53 and 54 at the entrance and exit of the primary chamber 44, the integrity of the flow path through the primary chamber can be monitored and, in particular, clotting of blood can be detected. In addition, if the return pressure detected by the third pressure sensor 54 is below a desirable level, disconnection of the return line 35 or the return catheter 36 may be indicated, which is treated as an alarm condition, as further described below.

A bubble detector 58 is connected in the primary circuit 38 downstream of the third pressure sensor 54. The bubble detector 58 is one of many known in the art and its function is to detect the presence of bubbles and microbubbles in the treated blood being returned to the patient 32 in the return line 35.

A return clamp 60 is also connected in the primary circuit 38 in order to selectively allow or terminate the flow of blood through the primary circuit established or regulated by the first pump 52 or by arterial blood pressure.

It is desirable when performing the various treatments using the apparatus 30 that anticoagulant be added to the blood in the primary circuit 38. The anticoagulant is added to the blood prior to its delivery to the primary chamber 44 in order to prevent undesirable coagulation of the blood resulting from contact of the blood with the semipermeable membrane 42 and other elements within the primary circuit 38. To add the anticoagulant a second pump 62 is connected to deliver anticoagulant from an anticoagulant container 64 along an anticoagulant line 65 to the blood prior to its entrance into the primary chamber 44. The anticoagulant container 64 is preferably a conventional syringe having a barrel and a plunger, and the pump 62 is a mechanical drive device to move the plunger into the barrel, thereby dispensing the anticoagulant into the blood of the primary circuit 38 in either a continuous or periodical basis. The anticoagulant container may also be a container connected to scales which weigh the content of the anticoagulant in the anticoagulant container. In this case, pump 62 is a peristaltic pump which delivers the anticoagulant from the anticoagulant container through the anticoagulant line 65.

It is sometimes desirable when performing certain treatments using the apparatus 30 that a replacement fluid be added to the blood in the primary circuit. The replacement fluid adds material to the blood in order to adjust the pH of the blood, to add nutrients to the blood, or to add fluid to the blood, among other reasons. A third pump 66 is connected in the primary circuit 38 at the exit of the blood from the primary chamber 44 and prior to returning the blood in the return line 35 to the patient 32. The third pump 66 delivers the replacement fluid from a replacement fluid container 68 through a replacement fluid line 70. The replacement fluid container 68 is connected to scales 72 which weigh the content of the replacement fluid within the replacement fluid container. Alternatively, the replacement fluid line 70 can be connected to the primary circuit 30 upstream of the primary chamber 44.

A secondary flow circuit 74 also interacts with the filtration unit 40. The secondary flow circuit 74 is connected to the secondary chamber 46. Matter extracorporeally added to the blood is delivered to the secondary chamber 46 through the secondary flow circuit 74, and matter extracorporeally removed from the blood is removed from the secondary chamber 46 through the secondary flow circuit 74. In some extracorporeal blood treatment protocols, all of the components of the secondary flow circuit 74 may not be used and/or functioning. The secondary flow circuit 74 includes the secondary chamber 46 of the filtration unit 40, a secondary fluid container 76, fourth pump 78, a secondary fluid line 80, a collection fluid line 82, fourth pressure sensor 83, a fifth pump 84, a leak detector 85 and a collection container 86.

The secondary fluid container 76 contains a sterile fluid, generally isotonic to blood, into which blood impurities will diffuse through the membrane 42 of the filtration unit 40. The pump 78 is connected in secondary fluid line 80 for delivering a secondary fluid from the secondary fluid container 76 into an entrance to the secondary chamber 46. The secondary fluid container 76 is connected to scales 90 which weigh the secondary fluid in the secondary fluid container.

The collection container 86 is provided to collect or receive matter from the blood transferred across; the semi-permeable membrane 42 and/or to receive the used secondary fluid after it has passed through the secondary chamber 46. The collection container 86 is connected to scales 92 which weigh the content of the collection fluid which has been collected in the collection container. The fifth pump 84 is connected to the collection line 82 for moving body fluid from the primary chamber 44 into the collection fluid container 86. The fourth pressure sensor 83 is also located in the collection line 82 for the purpose of monitoring the pressure in the secondary chamber. Also, plugging of the pores of the membrane 42 can be detected by monitoring the average pressure upstream and downstream of the filter as sensed by second and third pressure sensors 53 and 54, the pressure in the collection line 82 as sensed by fourth pressure sensor 83 and the actual flow rate of the collection fluid as measured by scales 92.

The leak detector 85 is also located in the collection line 82. The leak detector 85 is one of many known in the art and detects blood leaking into the secondary chamber by detecting blood in the collection fluid, typically by optical means.

Preferably, the filtration unit 40 and much of the flow tubing lines connecting the elements in the primary and secondary flow circuits 38 and 74 are formed as an integral, replaceable unit. Such an integral replaceable unit is described in greater detail in U.S. Patent Application for Integrated Blood Treatment Fluid Module referenced above. As is described in greater detail therein and as can generally be appreciated from FIGS. 1 and 2, the apparatus 30 includes a filtration unit retention device 94 which holds the filtration unit 40 in an operative position. When in the operative position, flexible fluid conducting lines to and from the filtration unit 40 are contacted by peristaltic pumping members of the pumps 52, 66, 78 and 84 to cause the fluid to flow through the primary and secondary circuits 38 and 74. The retention device 94 releases the filtration unit 40 from its operative connection to the device when treatment is completed.

The SCM system 48 of the apparatus 30 includes a control computer 102 and a monitor computer 104, as shown in FIG. 2. The primary function of the control computer 102 is to supply control signals to control the operation of the pumps 52, 62, 66, 78 and 84, to the return clamp 60 and to the retention device 94. The primary function of the monitor computer 104 is to monitor the functionality of the pumps 52, 62, 66, 78 and 84, the return clamp 60, the pressures sensed by pressure sensors 51, 53, 54, and 83, and the weights sensed by the scales 72, 90 and 92, by responding to monitor signals supplied to the monitor computer 104 from these components. The control and monitor signals may be selectively communicated between the two computers 102 and 104 through a dual ported memory 110. Although two computers 102 and 104 are utilized, it should be recognized that a single computer receiving all of the signals could be employed to achieve the same functions as described herein.

The control and monitor computers 102 and 104 are connected in control and monitor signal paths 106 and 108, respectively, with each of the pumps 52, 62, 66, 78 and 84, each of the scales 72, 90 and 92, the bubble detector 58 and return clamp 60. The pressure sensors 51, 53, 54, and 83 and the leak detector 85 are connected only to monitor signal path 108. Pressure monitor signals are derived by the pressure sensors 51, 53, 54, and 83 and are delivered over the monitor signal path 108 to the monitor computer 104. Pump monitor signals are derived from operation of the pumps 52, 62, 66, 78 and 84 and are also supplied over the signal path 108 to the monitor computer 104. Each of the scales 72, 90 and 92 derives weight monitor signals which are delivered over the signal path 108 to the monitor computer 104. Monitor signals from the leak detector 85, bubble detector 58 and return clamp 60 are also delivered over the signal path 108 to the monitor computer 104. Control signals from the control computer 102 are delivered over the control signal path 106 to the pumps 52, 62, 66, 78 and 84 to control their operation, to the bubble detector 58 to control the self-test thereof and monitor for bubbles, to the return clamp 60 to control its operation, and to the retention device 94 to control its operation. In addition, control signals derived by the scales 72, 90 and 92 are also supplied over the control signal path 106 to the control computer 102, since the signals supplied from the scales 72, 90, and 92 are used by the control computer 102 to assist in deriving the control signals supplied to the pumps 52, 62, 66, 78 and 84.

Selection of the treatment protocol and communication with the SCM system 48 is achieved by use of a input/output (I/O) device 112 which comprises a display 114 connected to the monitor computer 104 and a touch sensitive panel 116 connected to the control computer 102. Information concerning the functionality of the apparatus 30 is displayed to an operator through the display 114. Information and instructions from the operator are supplied to control computer 102 via the touch sensitive panel 116.

Figure 3A:
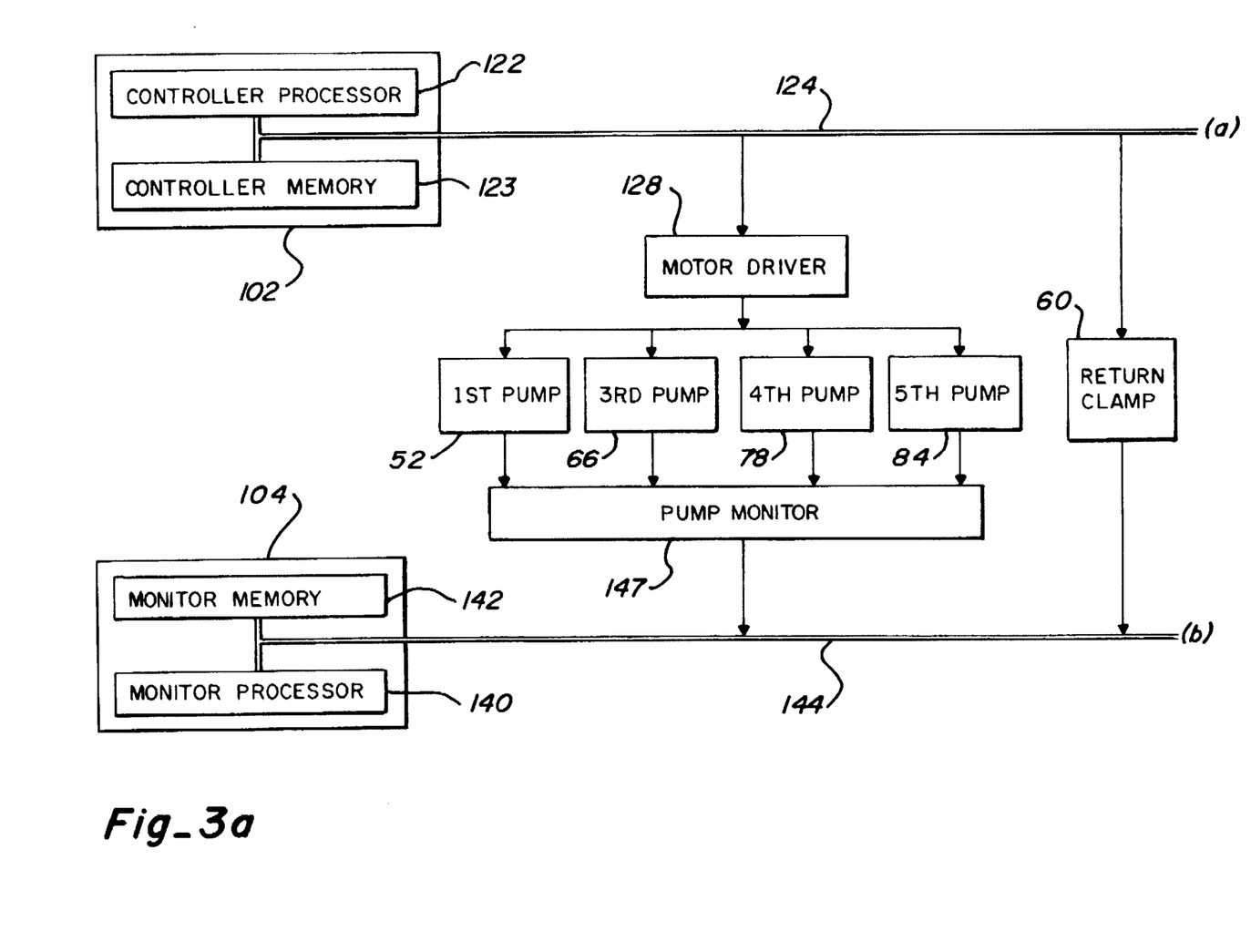
FIGS. 3a and 3b are an expanded block diagram of the components of a selection, control and monitoring system of the extracorporeal blood treatment apparatus shown in FIG. 2.
Figure 3B:
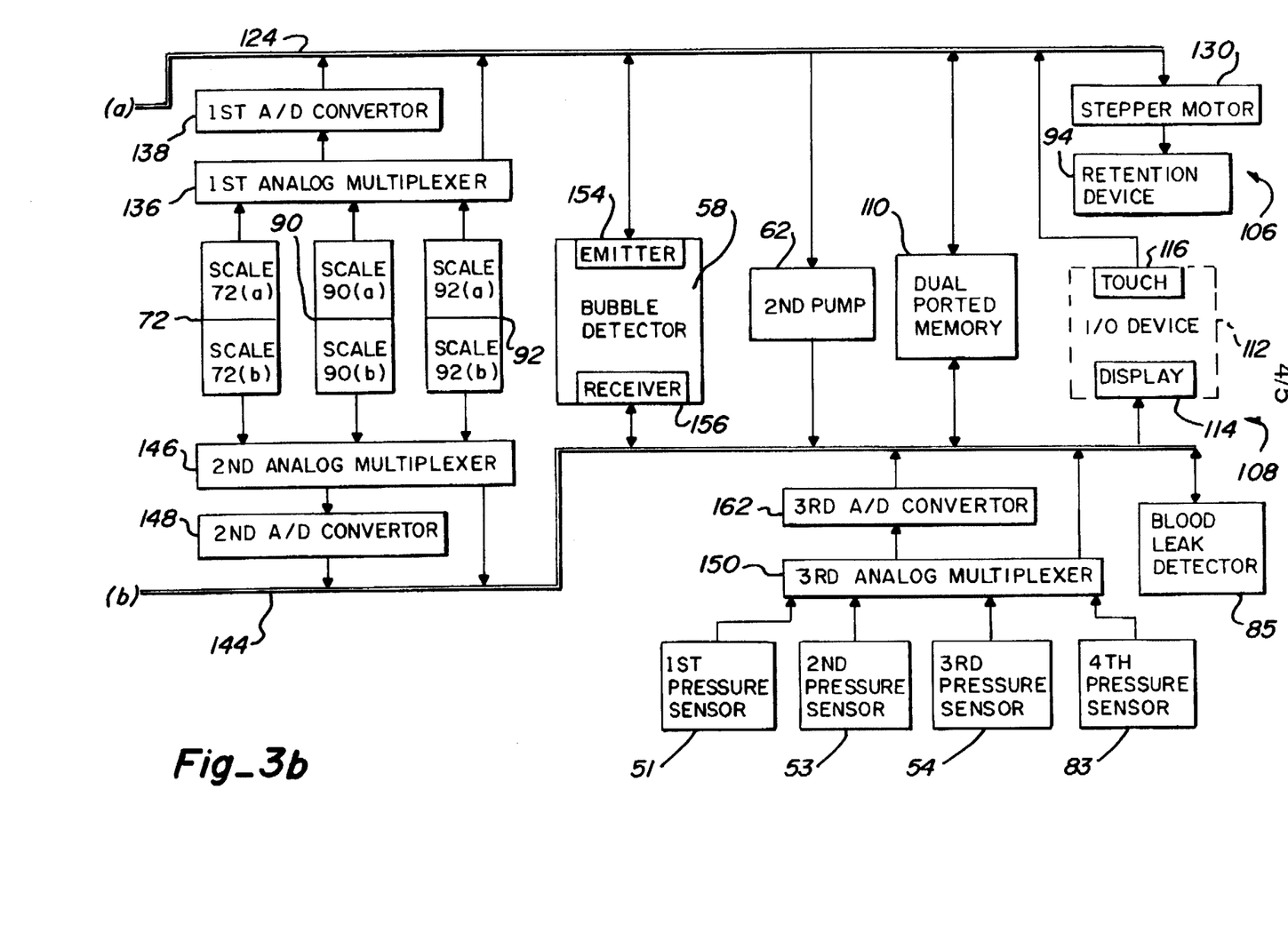

The signal paths 106 and 108 which conduct the control and monitoring signals to and from the components 50 of the apparatus 30 and the various components of the control and monitor computers 102 and 104 of the SCM system 48 and the interaction of the computers 102 and 104 with the other components 50 of the apparatus 30 to perform any one of a plurality of extracorporeal blood treatments are shown in greater detail in FIGS. 3a and 3b. The individual components of the control and monitor computers 102 and 104 are mounted on or installed inside a housing 120 (FIG. 1) of the apparatus 30.

The control computer 102 includes a control processor 122 and a control memory 123 connected by a control bus 124. As is conventional, the control processor 122 retrieves and stores instructions and data in the control memory 123, and while executing instructions utilizes data supplied to it over the bus 124 from the monitor computer 104 through the memory 110 and from some of the other components. The control signals are sent by the control processor 122 over the control bus 124. The control signal path 106 over which the control signals are sent includes the bus 124 and additional components which convert analog signals to digital signals when appropriate for interacting with the components 50 (FIG. 2). More details concerning the control signal path 106, the control signals conducted over the control path 106 and the operability of the control computer 102 obtained through communication of these signals is described below.

Signals are received by the control processor 122 over the control bus 124 from the touch panel 116 representing information or instructions from the operator about the treatment to be conducted or being conducted. The control processor 122 subsequently transmits signals over the control bus 124 to conduct or halt a treatment in accordance with the information and instructions.

The control processor 122 transmits signals over the control bus 124 to a conventional motor drive (circuitry) 128. The digital control signals supplied by the control processor 122 are received and interpreted by the motor controller 128 to select a particular one of the pumps 52, 66, 78 or 84 connected to the motor controller and to control the selected pump's operation, rate of operation and direction of operation.

As previously noted, the primary function of the first pump 52 is to control the rate of blood flow through the primary circuit 38 and to prime the primary circuit with a sterile solution prior to commencement of the treatment. If the treatment to be performed requires the introduction of replacement fluid into the blood before its return to the patient 32, the control processor 122 also sends signals over the control bus 124 to the motor driver 128 to the third pump 66 and the fifth pump 84 to cause the third pump 66 to dispense replacement fluid from the replacement fluid container 68 into the replacement fluid line 70 and thence to the return line 35 at a rate indicated by the signals and to cause the fifth pump 84 to remove the desired volume of body fluid. Additionally, if the replacement fluid line 70 is to be primed, appropriate signals from the control processor 122 to the third pump 66 about the direction and rate of pumping of the third pump can be transmitted over the control bus 124 to the motor driver circuitry 128. If the treatment to be performed requires a flow of secondary fluid into the secondary chamber 46, the control processor 122 also sends signals over the control bus 124 to the motor controller 128 to signal the fourth pump 78 to cause the fourth pump to dispense secondary fluid from the secondary fluid container 76 into the secondary fluid line 80 for introduction into the secondary chamber 46 at a particular pumping rate. If pumping by the fourth pump 78 is to be terminated, appropriate signals are sent by the control processor 122 over the control bus 124 to the motor controller 128.

All treatments require pumping by the fifth pump 84 to cause fluid in the secondary chamber 46 and, possibly, in the primary chamber 44, to be withdrawn into the collection line 82 and collected in the collection fluid container 86 at a desired rate. Signals about the rate and direction of pumping of the fifth pump 84 are also transmitted by the control processor 122 over the control bus 124 to the motor controller 128 to the fifth pump.

The control processor 122 also sends signals via the control bus 124 directly to the second pump 62 to cause a controlled release of anticoagulant into the primary circuit 38 to prevent undesirable coagulation of the blood in the primary chamber 44 and while flowing through the primary circuit 38.

The control processor 122 also sends signals over the control bus 124 to the return clamp 60 to open the return clamp when treatment is initiated so as to allow treated blood to be returned to the patient 32 and to close the return clamp when treatment is interrupted or terminated.

The control processor 122 transmits signals over the control bus 124 to a stepper motor driver 130 to activate a stepper motor and cause the retention device 94 to accept or release the filtration unit 40 and the primary and secondary fluid flow circuit conductors in the peristaltic pumps. Consequently, the filtration unit 40 and the primary and secondary fluid flow circuits 38 and 74 are maintained in position on the apparatus 30.

Control signals are also received by the control processor 122 relating to the weights of the containers 68, 76 and 86 detected by the scales 72, 90 and 92. Each of the scales 72, 90 and 92 comprises two parts "a" and "b", supplying two independent signals corresponding to the same container.

One part supplies signals to the control computer 102 and the other part supplies signals to the monitor computer 104. Initially, analog signals from the scales 72a, 90a and 92a representing the weight of the contents of the supply and collection containers 68, 76 and 86 (FIGS. 1 and 2) measured by the scales 72a, 90a and 92a are applied to a conventional first analog multiplexer 136. The multiplexer 136 connects a desired weight signal to a conventional first analog-to-digital (A/D) convertor 138. The first A/D convertor 138 converts the analog signal from the scale to a calibrated digital signal. The digital signal represents the weight measured by one of the scales 72, 90 or 92 and the identity of the scale from which the weight measurement originated and is sent to the control bus 124. In this manner the weight signal of the selected scale is made available to the control processor 122.

The signals from the scales 72a, 90a and 92a may be utilized by the control processor 122 to determine the weight of the particular fluid dispensed or collected. To determine the rate of fluid dispensing from or collecting into a particular container, the control processor 122 compares, at regular intervals (the higher the flow rate, the shorter the interval), the actual weight of the container to the desired weight. The desired weight can be calculated from the desired flow rate stored in the computer memory and the treatment time elapsed. If the actual weight and the desired weight differ, the control processor 122 controls the corresponding pump in order to decrease, and eventually to cancel, the difference. The control processor 122 takes into account the change in the difference since the latest comparison in order to avoid oscillations of the actual flow rate around the desired flow rate.

The monitor computer 104 includes a monitor processor 140 and a monitor memory 142 connected by a monitor bus 144. As is conventional, the monitor processor 140 retrieves and stores instructions and data in the monitor memory 142, and while executing instructions utilizes data supplied to it over the bus 144 from the control computer 102 through the memory 110 and from some of the other components. The monitor signals are sent by the components 50 to the monitor processor 140 over the monitor signal path 108. The monitor signal path 108 includes the bus 144 and additional components which convert analog signals to digital signals. More details concerning the monitor signal path 108, the monitor signals conducted over the path 108 and the operability of the monitor computer 104 obtained through communication of these signals is described below.

Signals are transmitted over the monitor bus 144 to the display 114 of the I/O device 112 to cause display of information about the treatment being performed derived from the monitor processor 140. Signals are also transmitted over the monitor bus 144 to the control processor 122 about the particular screen appearing on the display 114.

Monitor signals are received by the monitor processor 140 relating to the weights of the containers 68, 76 and 86 detected by the scales 72b, 90b and 92b. Initially, analog signals from the scales 72b, 90b and 92b representing the weight of the contents of the containers 68, 76 and 86 (FIGS. 1 and 2) are applied to a second analog multiplexer 146. The multiplexer 146 then connects the weight signal to a conventional second analog-to-digital (A/D) convertor 148. The second A/D convertor 148 converts the analog signal from the selected scale to a digital signal. The digital signal represents the weight measured by one of the scales 72b, 90b or 92b and the identity of the scale from which the weight measurement originated and is sent to the monitor bus 144. In this manner the weight signal of the scale is made available to the monitor processor 140.

The signals from the scales 72b, 90b and 92b may be utilized by the monitor processor 140 to determine the weight of the particular fluid dispensed or collected. To determine the rate of fluid dispensing from, or collecting into, a particular container, the monitor processor 140 compares, at regular intervals (the higher the flow rate, the shorter the interval), the actual weight of the container to the desired weight. The desired weight can be calculated from the desired flow rate stored in the computer memory and the treatment time elapsed. If the actual and the desired weight differ, the monitor processor 140 determines the flow rate of the corresponding pump, which will result in the decrease, and the eventual cancellation, of the difference, taking into account the change in the difference since the latest comparison.

Monitor signals include signals received by the monitor computer 104 over the monitor bus 144 from a pump monitor 149, a component of the signal path 108. During treatment each of the pumps 52, 66, 78 and 84 transmits signals to the pump monitor 149 about the rate of pumping of each of the pumps. When the pumps 52, 66, 78 and 84 are peristaltic pumps, the signals received by the pump monitor 149 may be digital signals indicating the number of revolutions of the pump 52, 66, 78 or 84 performed during a designated time period, which is indicative of the rate of pumping of the pump 52, 66, 78 or 84 so measured.

The pump 62 transmits signals directly to the monitor bus 144 about the rate of dispensing of anticoagulant. Whether the return clamp 60 is open or closed is also communicated to the monitor processor 140 over the monitor bus 144 via a signal from the clamp.

Monitor signals are received by the monitor processor 140 relating to the pressures detected by each of the first, second, third and fourth pressure sensors 51, 53, 54 and 83. Initially, analog signals from the pressure sensors 51, 53, 54 and 83 representing the pressure in primary and secondary circuits 38 and 74 (FIGS. 1 and 2) are applied to a conventional third analog multiplexer 150. The multiplexer 150 then connects the desired pressure measurement signal to a conventional third analog-to-digital (A/D) convertor 152. The third A/D convertor 152 converts the analog signal from the pressure sensor to a digital signal. The digital signal represents the pressure measured by the pressure sensors 51, 53, 54 and 83 and the identity of the pressure sensor from which the measurement originated and is sent to the monitor bus 144. In this manner the pressure measurement signal of the pressure sensor is made available to the monitor processor 140.

The signals from the pressure sensors 51, 53, 54 and 83 may be utilized by the monitor processor 140 to determine integrity of the primary and secondary circuits 38 and 74, and the condition of the semipermeable membrane 42, among other determinations. The determinations made by the monitor processor 140 are used to monitor the status of the apparatus 30 and the status of the treatment being performed. Based on these determinations, the monitor processor 140 reacts to perceived alarm conditions and notifies the operator about such alarm conditions by emitting an alarm and displaying information about the alarm, as is further described below.

When the pressure sensors 51, 53, 54 and 83 are of a conventional design comprising a disposable chamber connected to a nondisposable pressure transducer, the integrity of the pressure sensor chambers may be monitored by the monitor processor 140. Such pressure sensors have a flexible membrane located in the middle of the disposable chamber which divides the chamber into a first compartment in which the liquid to be measured flows, and a second compartment filled with air which is connected to the pressure transducer. A method for detecting the integrity of the pressure sensor chambers is further described below.

The monitor processor 140 is in two-way communication with the leak detector 85 via signals sent over the monitor bus 144. The leak detector 85, in cooperation with the monitor processor 140, conducts self-tests periodically to determine its operational integrity.

The monitor processor 140 and the control processor 122 are in two-way communication with the bubble detector 58 via signals sent over the monitor bus 144 and the control bus 124, respectively. The bubble detector 58 comprises a signal emitter 154 which transmits signals (preferably ultrasonic or light) through the blood flowing in the return line 35 to be received by a receiver 156 located on the other side of the return line. The signals are altered when bubbles or microbubbles are present in the line 35. Signals generated by the receiver 156 of the bubble detector and corresponding to either the absence of a bubble, or to a "big" bubble or to microbubbles, are supplied to the monitor and control processors 140 and 122. In addition, the control processor 122 sends signals regularly to the bubble detector 58 in order to test its operative integrity as to the detection of microbubbles and the monitor processor 140 regularly sends signals to the bubble detector 58 in order to test its operative integrity as to the detection of "big" bubbles. Each time either the control or monitor processor 122 or 140 initiates a test, it sends simultaneously a signal to the other processor to inform the other processor a test has been initiated.

Signals read by the monitor processor 140 about the treatment being performed including the rates of operation of each of the pumps 52, 62, 66, 78 and 84, the rate of fluid dispensing and collection, the status of the return clamp 60, the presence and volume of bubbles, the presence of blood leaks or of other conditions detected jeopardizing the safety of the treatment and other information are used to interpret alarm conditions.

A number of different protocols for extracorporeal blood treatment may be selected for performance by the apparatus 30. Those treatments include ultrafiltration (UF), hemofiltration (HF), hemodialysis (HD) and hemodiafiltration (HDF). In UF, blood is allow to pass through the primary chamber 44 of the filtration unit 40. Treatment is achieved when matter from the blood migrates across the semipermeable membrane 42 into the secondary chamber 46. Treated blood exiting the primary chamber 44 flows into the return line 35 for return to the patient 32. The rate of transfer of matter from the blood in the primary chamber 44 across a semipermeable membrane 42 into the secondary chamber 46 is determined in part by the rate of pumping of the fifth pump 84 which causes collection fluid exiting the secondary chamber 46 into the collection fluid line 82 to be removed to the collection fluid container 86. When UF is performed on blood controllably removed by the first pump 52 from a venous source of the patient, the treatment being conducted is slow continuous ultrafiltration (SCUF).

In HF, blood is treated as in UF, but in addition, replacement fluid is dispensed from the replacement fluid container 68 by action of the third pump 66 into the treated blood being returned to the patient, it being understood that while replacement fluid is described here as dispensed into treated blood, alternatively replacement fluid may be dispensed into blood prior to treatment in the filtration unit. Thus, to perform HF, the control processor 122 sends signals as described above to automatically operate the first, second, third and fifth pumps 52, 62, 66 and 84. The fourth pump 78 is not operated. When HF is performed on blood controllably removed by the first pump 52 from a venous source of the patient and is return to a venous return point, the treatment being conducted is continuous venovenous hemofiltration (CVVHF).

HD is performed if further control of the matter to be removed from the blood during treatment is desired or if matter is to be added to the blood during treatment. HD requires the dispensing of secondary fluid from the secondary fluid container 76 into the secondary fluid line 80 by pumping action of the fourth pump 78. As the secondary fluid passes through the secondary chamber 46 of the filtration unit 40, matter diffuses across the semipermeable membrane 42 into the blood and from the blood in the primary chamber 44. Collection fluid is then collected from the outlet of the secondary chamber 46 and pumped by the fifth pump 84 to the collection container 86. Thus, to perform HD, the control processor 122 sends signals as described above to automatically operate the first, second, fourth and fifth pumps 52, 62, 78 and 84. When HD is performed on blood controllably removed by the first pump 52 from a venous source of the patient and is returned to a venous return point, the treatment being conducted is continuous venovenous hemodialysis (CVVHD).

HDF involves the performance of HD and the addition of replacement fluid as in HF. To perform HDF, the control processor 122 sends signals as described above to cause the first, second, third, fourth and fifth pumps 52, 62, 66, 78 and 84 to automatically operate at desired rates. When HDF is performed on blood controllably removed by the first pump 52 from a venous source of the patient and is returned to a venous return point, the treatment being conducted is continuous venovenous hemodiafiltration (CVVHDF).

Information about the treatment protocol to be or being performed, the rates and direction of operation of each of the pumps 52, 62, 66, 78 and 84, the desired rate of fluid dispensing and collection, the desired rate of blood flow, and all the other information concerning each treatment protocol is stored in the memory 123, is modified by the operator or is newly input by the operator, in steps more fully described below. Based upon the desired rates, calculations are performed by the control processor 122 to determine a target rate of collection of collection fluid. For example, if a particular treatment protocol is not in memory, the operator enters in the desired rate of blood flow through the primary circuit, the rate of dispensing of anticoagulant (rate AC), the rate of dispensing of secondary fluid (rate D), the rate of dispensing replacement fluid (rate R), and the desired rate of removal of fluid from the patient (rate WL). Upon receipt of this information, the control processor 122 calculates the rate of collection of collection fluid (rate W) based upon the formula: W=WL+R+D+AC. (The rate AC may be disregarded if the rate AC is determined to be negligible.) Alternatively, if a particular protocol is already in memory, the blood flow rate and the rates AC, D, R, and WL will be retrieved from the control memory 123 and the rate W calculated. If these values are deemed by the operator to be satisfactory, the operator accepts the values, as further described below. If, however, the operator desires to modify one or more of the rates, the operator inputs the modified rate(s) via the touch panel 116 and the control processor 122 calculates the revised collection fluid flow rate W.

During treatment, based upon the rate information collected and calculated as above, each of the pumps 52, 62, 66 and 78 is individually and controllably operated by the control computer 102 to maintain the rates in accordance with the rate information, as previously described. However, the rate of operation of the fifth pump during treatment is determined during treatment by the control processor 122 comparing the rate W being achieved during treatment with the desired rate W previously calculated.

Figure 4:
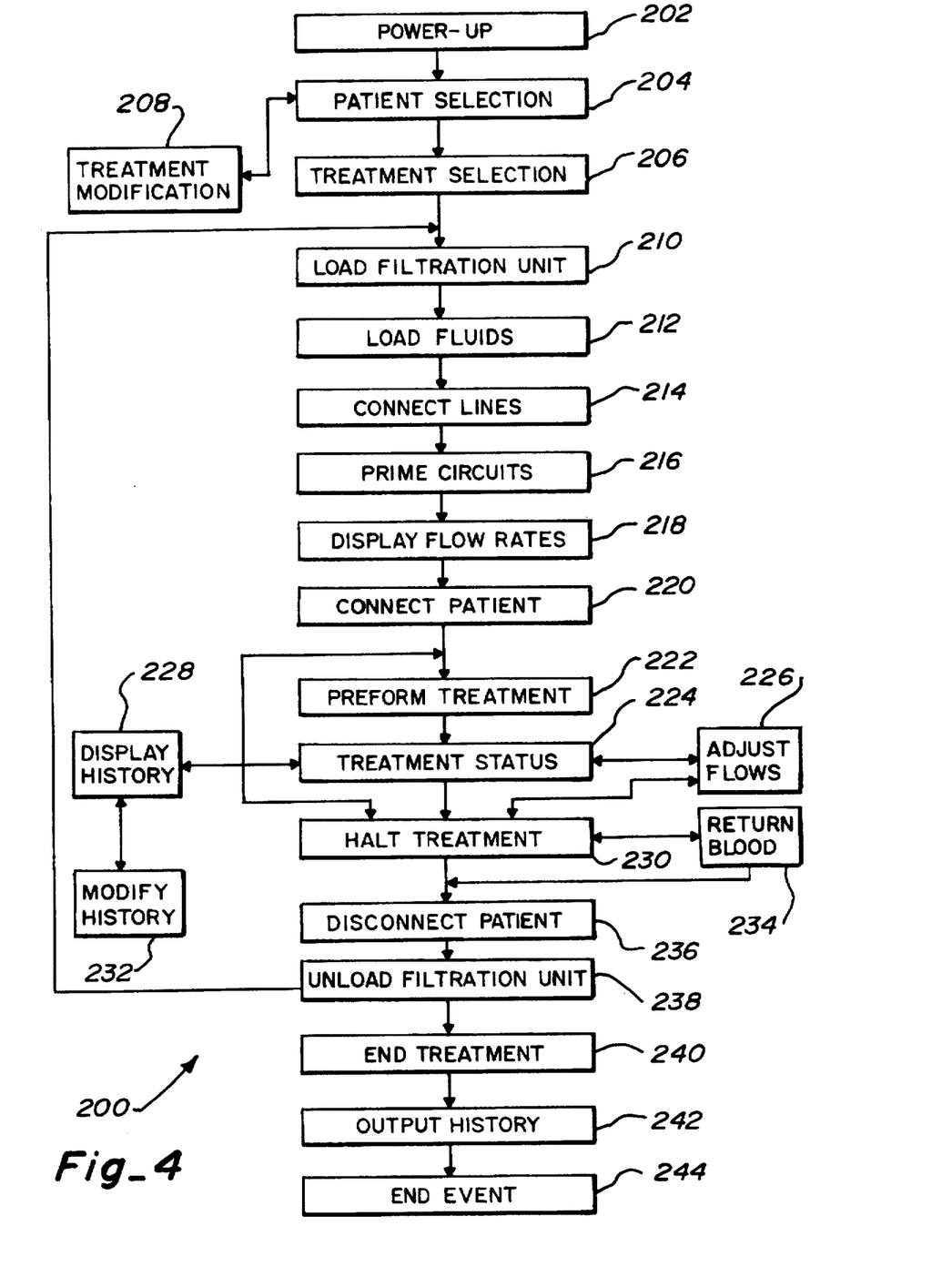
FIG. 4 is a flow chart showing the functionality of the extracorporeal blood treatment apparatus of FIGS. 1, 2, 3a and 3b, and the treatment steps involved in practicing the methodology of the present invention.

To select, set or modify one of the treatment protocols, the operator supplies input information to the control computer 102 through the I/O device 112. The flow chart 200 of FIG. 4 represents the steps performed during the selection and performance of the treatment protocols. For convenience, each step is referenced by a designated number. Each step may also be described as being performed in conjunction with components described in FIGS. 1, 2, 3a or 3b. References to the components in FIGS. 1, 2, 3a and 3b are made in conjunction with the description of the steps shown in FIG. 4.

The power-up step 202 occurs upon starting the apparatus 30 and allows the operator to indicate a readiness to proceed with setting up the apparatus 30 for treatment of a patient 32. The operator communicates that readiness and all other instructions and information to the control processor 122 by input signals resulting from touching the touch panel 116 of the I/O device 112.

Upon receipt of the signal to proceed, a patient selection step 204 is performed. The patient selection step 204 allows the operator to supply information via the touch panel 116 and choose to either identify a patient for which treatment has been just previously performed and thereby retain that patient's operating parameters information previously stored to the control memory 123, to erase previous information to start a new patient, to add new treatment protocols, or to select and modify treatment protocols previously stored. If the operator selects the same patient about which treatment information is previously stored, the functionality proceeds to a treatment selection step 206.

If the operator desires to perform a treatment on a new patient, old data are deleted from memory and information about the new patient is input via the touch panel 116 and is automatically stored in the control memory 123, after which the functionality proceeds to the treatment selection step 206.

If the operator chooses to modify a pre-existing or pre-programmed treatment protocol, the treatment modification step 208 is performed. During the treatment modification step 208, parameters about a treatment previously stored to the control memory 123 are retrieved and are modified by operator input, with the modified treatment protocol automatically then being stored in memory. Such parameters include types and rates of fluids to be dispensed during treatment, rate of collection of collection fluid, blood flow rate, pressures levels to be maintained in the primary and secondary circuits 38 and 74, frequency of replacement of the filtration unit 40 and duration of treatment, for example. In addition to treatments previously stored, new treatment protocols may be added and stored in the control memory 123. New treatment protocols can incorporate a previously stored treatment protocol for which parameters are modified for a different class of patients, such as the parameters for performing CVVH in children weighing between 60 and 70 pounds. After the treatment modification step 208 has been performed, the functionality returns to the patient selection step 204 and then moves to the treatment selection step 206.

The treatment selection step 206 allows the operator to select the treatment to be performed by the apparatus 30, such as, for example, choosing from among SCUF, CVVH, CVVHD and CVVHDF. Once the treatment has been selected, operation will continue based upon the treatment parameters associated with the selected treatment. Functionality then proceeds automatically to the load filtration unit step 210.

During the load filtration unit step 210, the operator is instructed via the display 114 about how to load the filtration unit 40 in the retention device 94 and the tubes of the primary and secondary circuits 38 and 74 into the pumps 52, 66, 78 and 84 when the filtration unit and the primary and secondary circuits are integrally connected as part of the filtration unit 40 (FIGS. 1 and 2). The retention device is extended automatically to accept the filtration unit 40 and the primary and secondary circuits 38 and 74. Upon receipt from the operator of touch panel 116 input, the retention device 94 receivably retains the filtration unit 40 and the primary and secondary circuits 38 and 74 in place and loading is complete. Functionality then proceeds automatically to the load fluids step 212.

During the load fluids step 212, the operator is instructed from instructions preprogrammed in memory via the display 114 about which fluids to provide to perform the selected treatment. For example, if any of SCUF, CVVH, CVVHD, or CVVHDF is to be performed, the operator is instructed to provide an anticoagulant if desired. If CVVH or CVVHDF is to be performed, the operator is instructed to provide replacement fluid. If CVVHD or CVVHDF is to be performed, the operator is instructed to provide secondary fluid. Once the fluids in their containers are appropriately loaded onto the scales 72, 90 and 92 (FIGS. 1 and 2), the operator instructs the functionality to continue, at which point functionality proceeds automatically to the connect lines step 214.

During the connect lines step 214, the operator is instructed via the display 114 about which lines to connect to which fluid containers. For example, if any of SCUF, CVVH, CVVHD or CVVHDF is to be performed, the operator is instructed to connect the line from the anticoagulant container 64, if used, to the access line 34 and the collection line 82 from the secondary chamber 46 to the collection container 86. If CVVH or CVVHDF is to be performed, the operator is instructed to connect the replacement fluid line 70 to the replacement fluid container 68. If CVVHD or CVVHDF is to be performed, the operator is instructed to connect the secondary fluid line 80 to the secondary fluid container 76. Once the lines are appropriately connected, further operator instruction causes the functionality to automatically proceed to the prime circuits step 216.

During the prime circuits step 216, the operator is instructed via the display 114 about priming the primary and secondary circuits 38 and 74. For all treatment protocols, the second pump 62 is automatically signalled by the control processor 122 to pump anticoagulant into the line in which anticoagulant is dispensed into the access line 34. For all treatment protocols the operator is instructed to provide priming solution to the primary circuit 38 by connecting a priming liquid container to return line 35 and a collection container to the access line 34.

The priming of the primary circuit 38 is performed by continuously operating the first pump 52, throughout the prime circuits step 216, in a reverse direction with respect to its operation during the treatment. The priming of the remaining circuits (secondary circuit 74 and replacement fluid line 70) is performed differently depending on the treatment protocol selected. If the treatment protocol selected in UF, after the primary circuit 38 is filled with priming fluid, the fifth pump 84 is operated in the same direction as during the treatment until the end of the prime circuits step 216. As a consequence, priming fluid is ultrafiltered through the membrane 42 from the primary chamber 44 of the filter 40 into the secondary chamber 46 and is circulated into the collection container 86. Also, when the primary circuit 38 is filled with priming fluid, the third pump 66 is operated for a fraction of the time of the prime circuit step 216, in a reverse direction with respect to its operation during the treatment. The third pump 66 thus partially fills the replacement fluid line 70 so that no blood/air interface occurs during the treatment at the connection between the primary circuit 38 and the replacement fluid line. Similarly, when the secondary chamber 46 is filled with priming fluid, the fourth pump 78 is operated for a fraction of the time of the prime circuit step 216, in a reverse direction with respect to its operation during the treatment, in order to partially fill the secondary fluid line 80.

If the treatment protocol selected is HF, the priming process is the same as previously described, except as to the replacement fluid line 70. Since a replacement fluid container 68 is now connected to the replacement fluid line 70, the priming of this line is performed by circulating replacement fluid from the container 68 into the primary circuit 38, operating the third pump 66 in the same direction as during the treatment for a fraction of the time of the prime circuit step 216.

If the treatment protocol selected is HD, the priming process is the same as described for UF, except as to the secondary fluid line 80. Since a secondary fluid container 76 is now connected to the secondary fluid line 80, the priming of this line is performed by circulating secondary fluid from the container 76 into the secondary chamber 46, operating the fourth pump 78 in the same direction as during the treatment for a fraction of the time of the prime circuit step 216.

If the treatment protocol selected is HDF, the priming process is the same as described for HD, except as to the replacement fluid line 70. Since a replacement fluid container 68 is now connected to the replacement fluid line 70, the priming of this line is performed by circulating replacement fluid from the container 68 into the primary circuit 38, operating the third pump 66 in the same direction as during the treatment for a fraction of the time of the prime circuit step 216.

Whatever the priming process performed, it ends with a priming test comprising the steps of:

1) clamping the return line 35 with the return clamp 60;
2) operating the first pump 52 in the same direction as during the treatment, for a determined period of time;
3) checking that the pressure in the primary circuit 38 between the first pump 52 and the return clamp 60 has reached a predetermined threshold and remains above this threshold all over the priming test;
4) indicating an alarm if one of the conditions of step three is not realized;
5) operating the first pump 52 in a reverse direction in order to compensate its previous operation; and
6) opening the return clamp 60. Steps 1, 2, 5, 6 of the priming test are performed by control processor 122 and steps 3, 4 are performed by monitor processor 140. After priming is complete, the functionality automatically proceeds to the display flow rates step 218.

The display flow rates step 218 involves the display of flow rates to be achieved with the treatment selected on the display 114. Further operator instruction to continue at this point causes the functionality to automatically proceed to the connect patient step 220.

During the connect patient step 220, the operator is instructed to connect the access line 34 and the return line 35 to the patient 32. Once the lines 34 and 35 are appropriately connected, further operator instruction to continue at this point automatically causes the performance of the treatment step at 222.

During the perform treatment step 222, treatment commences in accordance with the treatment protocol selected. The ones of the pumps 52, 62, 66, 78 and 84 are operated as preprogrammed, effectively treating blood in the primary circuit 38, dispensing fluids into the primary circuit, and pumping secondary fluid as required into the secondary circuit 74 and collecting collection fluid from the secondary chamber as appropriate. Once treatment is initiated, functionality proceeds automatically to the treatment status step 224.

During the treatment status step 224, the apparatus 30 automatically continues performing the treatment protocol previously selected in accordance with the parameters associated with that protocol and displays information about the treatment on the display 114. At this point, the apparatus 30 is responsive to operator input to proceed to the adjust flows step 226, during which treatment typically continues, to a history display step 228 during which treatment typically continues, or to a halt treatment step 230. If the operator chooses to proceed to the adjust flows step 226, one or more flow rates may be changed. Once the new flow rate is input by the operator, the control processor 122 automatically recalculates new flow rates affected by the operator input. In the case when the resultant blood ultrafiltrate flow rate exceeds a predetermined percentage (20% for example) of the blood flow rate, the operator is so notified. Otherwise, upon completion of the adjust flows step 226, the functionality is returned to the treatment status step 224 and the new flow rates are automatically acted upon by the control processor 122 with the selected treatment proceeding accordingly.

If the operator chooses the display history step 228, a history of the treatment being performed is displayed on the display 114. The processors 122 and 140 are responsive to operator input to proceed to the modify history step 232 or to return to the treatment status step 224. During the modify history step 232, parameters controlling the display of treatment history may be modified by the operator. After completing such modifications the control processor 122 is responsive to operator input to return to the display history step 228 and thence to the treatment status step 224.

The functionality proceeds to the halt treatment step 230 as a result of operator request and as a result of detection of alarm conditions by either processor. During the halt treatment step 230, the ones of the pumps 52, 62, 66, 78 and 84 which have been operating are automatically instructed by signals transmitted by the control processor 122 to the motor controller 128 to cease pumping. If the operator elects to proceed to the return blood step 234, the operator is instructed to return the blood in the primary circuit 38 through the return line 35 to the patient 32. When the blood return step is complete, the functionality proceeds automatically to the disconnect patient step 236.

During the disconnect patient step 236, the control processor 122 automatically causes the return clamp 60 to close, if the return clamp 60 has not already been closed as part of an automatic response to an alarm condition. The operator is then instructed to disconnect the access and return lines 34 and 35 from the patient 32. When disconnection of the patient is complete, the functionality proceeds to the unload filtration unit step 238.

During the unload filtration unit step 238, the operator is instructed via the display 114 about how to unload the primary and secondary circuits 38 and 74 and the filtration unit 40 from retention device 94 and the pumps 52, 66, 78 an 84. Disconnection is accomplished when the control processor 122 sends signals to cause the retention device 94 to automatically release the filtration unit. Once the unload filtration unit step 238 is complete, the control processor is responsive to operator instructions to return to the load filtration unit step 210, in which case the operator will effectively proceed with replacing the primary and secondary circuits 38 and 74 and the filtration unit 40 so as to continue in accordance with the steps of the flow chart 200. Alternatively, the processors 122 are responsive to instructions to end treatment the treatment at step 240.

The end treatment step 240 includes an automatic calculation of treatment data by the control processor 122. Upon responsive input from the operator, the control processor 122 causes the functionality to proceed to the output history step 242. If the apparatus 30 has a printer (not shown) attached to any of the busses 124 or 144, the history of the treatment performed can be printed for retention in the patient's file. In any case, the history of the treatment performed can be displayed on the display 114 of the I/O device 112. The control processor 122 is responsive to operator input to proceed to the end event step 244 at which point the apparatus 30 may be powered off.

When the control processor 122 receives signals from the monitor processor 140 about critical conditions in which the patient may be at risk while at step 226 as shown in FIG. 4, the control processor transmits signals via the control bus 124 to the motor controller 128 to instruct each of the pumps 52, 66, 78 and 84 which has open operating to halt, to instruct the second pump 62 to stop dispensing anticoagulant, to instruct the return clamp 60 to close, at which point the apparatus is considered to be in a "safe state." The control processor 122 also sends signals as appropriate to cause the status lights 126 to indicate the apparatus 30 has been put into a "safe state." The monitor processor 140 is notified that the apparatus 30 has entered a safe state via signals from the control processor 122 transmitted over the control bus 124, to the dual ported memory 110 and the monitor bus 144. The monitor processor 140 also causes an audible alarm to be emitted. The various alarm conditions, operator options and mechanical responses are described in more detail below.

One serious alarm condition, disconnection of the patient's return catheter, is suspected if the monitor processor 140 receives signals from the third pressure sensor 54 that pressure in the return line 35 is lower than a predetermined value stored in the monitor memory 142. Another serious alarm condition, disconnection of the access line 34 between the first pump 52 and the inlet port of the primary chamber 44, is suspected if the monitor processor 140 receives signals from the second pressure sensor 53 that pressure in the access line 34 is more negative than a predetermined value stored in the monitor memory 142. Yet another serious alarm condition, disconnection of the access catheter at its connection to the access line 34 is suspected if the monitor processor 140 receives signals from the first pressure sensor 51 that pressure in the access line is more positive than a predetermined value stored in the monitor memory 142. If any of these conditions are detected, signals are sent to the control processor 122 via the dual ported memory 110 so that the control processor can send appropriate signals to cause the apparatus 30 to enter its safe state. The operator is notified of the situation via the display 114 and via an audible alarm. Using the touch panel 116, the operator can instruct the control processor 122 to proceed to the flow adjustment step 226, to the disconnect patient step 236 (without performing the return blood step 234), or to override the alarm and continue treatment. In the latter case, the above alarm conditions is rechecked after a predetermined amount of time.

The monitor processor 140 also signals an alarm condition if it detects the filtration unit 40 is clotted. Filter clotting is suspected if the monitor processor 140 receives signals from the fourth pressure sensor 83 that are more negative than a predetermined value stored in the monitor memory 142. If filter clotting is suspected, the monitor processor 140 transmits signals to the control processor 122 to put the apparatus 30 in its safe state. The operator is notified via the display 114 and via an audible alarm. Using a touch panel 116 the operator can proceed to the disconnect patient step or may instruct the control processor 122 to continue treatment, in which case the monitor processor 140 determines if the alarm condition has been remedied and if remedied, notifies the control processor 122 to release the return clamp 60 and begin operating the pumps 52, 62, 66, 78 and 84 in accordance with the previously selected treatment.

If the monitor processor 140 receives signals from the leak detector 85 indicating a leakage of blood across the membrane of the filtration unit 40, the monitor processor will send signals via the dual ported memory 110 to the control processor 122 so that the control processor may put the apparatus 30 in its safe state. The operator is notified of the situation via the display 114 and via an audible alarm, and using the touch panel 116, can instruct the control processor 122 to override the alarm and continue treatment in which case the alarm condition is rechecked after a predetermined time, or can proceed to the disconnect patient step 240.

If the monitor processor 140 receives signals from the bubble detector 58 that one or more full-size bubbles have been detected, the monitor processor will send signals via the dual ported memory 110 to the control processor 122 so that the control processor may put the apparatus 30 in its safe state. The operator is notified of the situation via the display 114 and via an audible alarm, and using the touch panel 116, can instruct the control processor 122 to override the alarm and continue treatment in which case the alarm condition is rechecked immediately after the instruction is given, or can proceed to the disconnect patient step 236.

If the monitor processor 140 receives signals from the bubble detector 58 indicating that the total volume of gases in the form of microbubbles carried in the return blood during treatment meets or exceeds a predetermined volume stored in the monitor memory 142, the monitor processor will send signals via the dual ported memory 110 to the control processor 122 to put the apparatus 30 in its safe state. The operator is notified of the situation via the display 114 and via an audible alarm, and using the touch panel 116, can instruct the control processor 122 to override the alarm and continue treatment, or can select proceed to the disconnect patient step 236.

In a custom mode, the operator can set a return blood pressure maximum above which an alarm condition is detected and an access pressure minimum below which an alarm condition is detected, while at the adjust flow step 226 shown in FIG. 4. If the monitor processor 140 detects that the access pressure measured by the first pressure sensor 54 falls below the minimum pressure previously set and stored in control and monitor memories 123 and 142 or that the return pressure measured by the third pressure sensor 54 rises above the maximum pressure previously set and stored in memory, signals are sent to the control processor 122 via the dual ported memory 110 so that the control processor can send appropriate signals to cause the apparatus 30 to enter the safe state. The operator is notified of the situation via the display 114 and via an audible alarm. Using the touch panel 116, the operator can instruct the control processor 122 to make adjustments to treatment flow rates via the flow adjustment step 226, to proceed to the disconnect patient step 236 (without executing the return blood step 234) or to override the alarm and continue treatment. In the latter case, the above alarm conditions is rechecked immediately after the instruction is given.

In addition to the first class of most serious alarm conditions just described, a second class of alarms indicates possible malfunction in the apparatus 30. If a malfunction condition is detected, the monitor processor 140 sends signals via the monitor bus 144 through the dual ported memory 110 over the control bus 124 to the control processor 122 notifying the control processor of the particular malfunction. The monitor processor 140 also sends signals to the display 114 and via an audible alarm to notify the operator of the malfunction alarm. Meanwhile, the control processor 122 sends signals over the control bus 124 to the motor controller 128 instructing it to send signals to each of the pumps 52, 66, 78 and 84 to halt, to the return clamp 60 to close and occlude the return line 35, and to the second pump 62 to cease dispensing anticoagulant. The particular malfunction alarm condition is retained in memory in the control memory 123 and the monitor memory 142 which detect that the apparatus 30 has been powered off so that the malfunction condition can be serviced. Once powered back up, the alarm will clear upon detection by the monitor processor 140 that the malfunction condition is no longer present. Various malfunction conditions and possible operator responses are described in more detail below.

If either processor detects a failure in the bubble detector 58 self-tests, or if the monitor processor 140 detects a failure in the leak detector 85 self-test, it sends signals to the control processor 122 notifying it of this malfunction, in which case the control processor sends signals as appropriate to put the apparatus 30 in its safe state. The selections available to the operator on the display 114 include disconnecting the patient without returning treated blood to the patient, disconnecting the patient after returning the blood to the patient, or continuing the testing of the bubble detector 58 or leak detector 85, as appropriate.

If the monitor processor 140 detects that the return clamp 60 is open when it should be closed or that it is closed when it should be open, it sends signals to the control processor 122 notifying it of this malfunction, in which case the control processor sends signals as appropriate to put the apparatus 30 in its safe state. The operator can proceed to the disconnect patient step 236 or can return to the status step 224 in which case treatment will continue after the monitor processor 140 determines that the malfunction has been remedied.

If the monitor processor 140 detects that one of the pumps 52, 66, 78 or 84 is not pumping at the expected rate (whether such rate is that initially retrieved from the control memory 123 or has been modified by the operator), the monitor processor signals the control processor to put the apparatus 30 in a safe state. If the malfunction is detected in the pumps 66, 78 or 84, the operator may choose to override the malfunction alarm, in which case the apparatus 30 must be powered off and on and the treatment continued via appropriate selection on the touch panel 116 or may choose to disconnect the patient with or without returning treated blood to the patient. If, however, the first pump 52 is detected to be malfunctioning, disconnection can only occur without returning of treated blood to the patient.

If the monitor processor 140 detects that the second pump 62 is not dispensing anticoagulant at the expected rate, the control processor 122 is instructed to put the apparatus 30 in a safe state. The operator may select, via the touch panel 116, to proceed to the flow adjustment step 226 and proceed to modify the rate for the second pump 62. When modifications are complete, information about the alarm is redisplayed on the display 114. Alternatively, the operator may choose to proceed to the disconnect patient step 236 or to return to the status step 224, in which case the monitor processor 140 will determine if the alarm condition has been remedied and will signal the control processor 122 to continue treatment if the condition is remedied.

If the monitor processor 140 determines that the weight reported by the control processor 122 for one of the containers 72, 90 and 92 is different than the weight detected by the monitor processor, it sends signals to the control processor 122 notifying it of this malfunction. The control processor 122 then sends signals as appropriate to put the apparatus 30 in its safe state. The operator can proceed to the disconnect patient step 236 or can continue in the halt step 230 mode, with weighing continuing until the condition has been fixed, at which point treatment will continue with the status step 224.

If the monitor processor detects a failure in a pressure sensor self test, it sends signals to the control processor 122 notifying it of this malfunction, in which case the control processor sends signals as appropriate to put the apparatus 30 in its safe state. The operator can then proceed to the disconnect patient step 236 (without proceeding to the return blood step 234) or can override alarm and return to the status step 224, in which case treatment will continue and the monitor processor 140 will recheck the malfunction condition after a predetermined period.

Other malfunctions also cause the monitor processor 140 to instruct the control processor 122 to put the apparatus 30 in its safe state but the safe state can only be cleared by servicing the apparatus 30. Such malfunctions include detection by the control processor 140 that a key of the touch panel 116 is malfunctioning, that the screen appearing on the display 114 as reported by the control processor 122 does not match the screen reported by the monitor processor 104, that either the control processor 122 or the monitor processor 140 has been reset too many times in a predetermined period, or that there has been a failure in the control memory 123, the monitor memory 142 or in the dual ported memory 110.

Other malfunctions also cause the monitor processor 140 to instruct the control processor 122 to put the apparatus 30 in its safe state but can be remedied without disconnection of the patient. Such malfunctions include detection by the monitor processor 140 that one of the sensors 51, 53, 54 or 83 or one of the scales 72, 90 or 92 has failed a self test. In each case, if the operator chooses to continue, the monitor processor 140 retests the malfunctioning unit and signals the control processor 122 to continue treatment when the malfunction has been corrected.

In addition to the most serious alarm conditions and the malfunction alarms previously described, a third class of alarms, referred to herein as caution alarms, indicates possible incorrect treatment administration with the apparatus 30. Upon detection by the monitor processor 140 of conditions constituting a caution alarm, the monitor processor notifies the control processor 122 of the condition which instructs the pumps 52, 66, 78 and 84 to halt, also causes the display 114 to update the operator, and may emit an audible alarm.

Caution alarms include detection by the monitor processor 140 that the weight of collection fluid in the collection container 86 does not match the volume expected from the previously selected flow rates, that the weight of replacement fluid in the replacement fluid container 68 does not match the volume expected from the previously selected flow rates, that the weight of secondary fluid in the secondary fluid container 76 does not match the volume expected from the previously selected flow rates, or that the pores of the semipermeable membrane 42 are becoming clogged. In each case, the operator can choose via the touch panel 116 the responses available at the halt treatment step 230. If the operator elects to override the caution alarm, the monitor processor 140 rechecks the alarm condition in a predetermined amount of time previously stored in the monitor memory 142.

If one of the pumps 52, 66, 78 or 84 moves while the apparatus 30 is in a safe state, the movement is detected by the monitor processor 140 which signals the control processor to cut power to the pumps 52, 66, 78 and 84. The operator can select to override the malfunction alarm, in which case the apparatus 30 must be powered off and on and the treatment continued via appropriate selection on the touch panel 116. Alternatively, the operator may notify the control processor 122 through the touch panel 116 of an intent to disconnect the patient.

The third class of alarms also includes detection by the monitor processor 140 that the collection container 86 is full, or that the replacement fluid container 68 or the secondary fluid container 76 is empty. An alarm message is displayed on the display 14 and the operator is instructed to empty, replace or fill the appropriate container. Treatment is automatically halted at the halt treatment step 230. If the operator elects to continue treatment and has replaced the container 68, 76 or 86 responsible for the caution alarm and the monitor processor 140 will detect the alarm condition has been is cleared and will instruct the control processor 122 to continue treatment.

It is also considered a caution condition when the rate of fluid removal is too high, given the selected blood flow rate. In this case, the alarm is displayed on the display 114 and the treatment proceeds to the adjust flows step 226. The operator can, alternatively, elect to proceed to the disconnect patient step 236 or to the status step 224 in which case treatment is continued and the alarm condition rechecked.

A fourth class of alarms, called herein advisory alarms, are detected by the monitor processor 140, which advises the operator of the condition via the display 114 (and also may advise the operator via an audible alarm) and notifies the control processor 122 of the condition via signals over the monitor bus 144, the dual ported memory 110 and the control bus 124. Treatment is allowed to continue until such time as the operator inputs via the touch panel 116 instructions to the control processor 122 on a subsequent course of action. The selections available for some advisory alarm conditions are described below.

If the monitor processor 140 cannot effectively monitor pressure with the first, second, third or fourth sensors 51, 53, 54 and 83 because the blood flow rate is too low, and thus cannot detect access line 34, return line 35 or other primary circuit 38 disconnections, the operator can elect to override the alarm or proceed to the adjust flow step 226 and adjust one or more of the flow rates, after which the alarm display will reappear on the display 114. If the operator elects to override the alarm, treatment continues with the advisory alarm clearing only when the monitor processor 140 detects that the previously detected low pressure measurement has become more positive by a previously determined amount.

Advisory alarms detected during the priming step 216 include detection by the monitor processor 140 that the collection container 86 is full or that the secondary or replacement fluid containers 76 and 68 is empty. The operator is notified of the condition via the display 114. Upon receipt of an operator instruction to continue via the touch panel 116, the monitor processor 140 rechecks the condition and clears the alarm display if the condition has cleared.

If the monitor processor 140 detects that the anticoagulant container 64 is empty, the operator may elect to proceed to the flow adjustment step 226 and adjust the anticoagulant flow rate, after which the advisory alarm is redisplayed on the display 114. Alternatively, the operator may elect to continue therapy, at which point the alarm condition is rechecked and the alarm display cleared if the condition has been fixed.

If the monitor processor 140 detects that any one of the scales 72, 90 or 92 has been disturbed, the operator is so advised via the display 114. The monitor processor 140 automatically clears the display 114 when the condition has been corrected or when the operator inputs a continue command via the touch panel 116.

If the monitor processor 140 detects a power loss while data is being updated by the control or monitor processors 122 and 140, the operator is so advised via the display 114. The monitor processor 140 clears the display 114 when the operator acknowledges the message by inputting a continue command using the touch panel 116.

Preferably the apparatus 30 should have periodic preventive maintenance conducted to assure reliability while performing treatments. A preventive maintenance interval is stored in monitor memory 142. If the monitor processor 140 detects that the stored interval has elapsed, the operator is apprised of the condition via a message on the display 114. The monitor processor 140 clears the display 114 when the operator acknowledges the message by inputting an override command using the touch panel 116. This advisory alarm is cleared when the apparatus 30 is placed in a service mode.

If the monitor processor 140 detects that the filter 40 is beginning to clot or that the particular primary circuits 38 has been used for a predetermined period of time, the operator is advised of the condition via the display 114. The operator can then elect, via appropriate input to the touch panel 116, to proceed to the halt treatment step 230 and thence to the disconnect patient step 236 and the unload filtration unit step 238. The operator can then elect, as previously described, to proceed to the end treatment step 240 or may load new circuitry, in which case the operator proceeds to the load circuit step 120. Alternatively, the operator may elect to override the advisory and continue treatment. In either case, the monitor processor 140 clears the alarm display from the display screen 114 when the circuits have been unloaded, or when the clotted filter alarm occurs.

If treatment with the apparatus 30 has been stopped for more than a predetermined period of time previously stored to the monitor memory 142, the operator is advised of the condition via the display 114 by the monitor processor 140.

The operator can to enter proceed to the disconnect patient step 236 or may elect to continue treatment and continue the status step 224, in which case the monitor processor 140 clears the display 114 of the advisory message.

If the monitor processor 140 detects via signals from the third pressure sensor 54 that pressure in the return line 35 has fallen a predetermined amount below initial operating conditions, the operator is notified via an advisory alarm to the display 114. The operator is similarly notified if the monitor processor 140 detects via signals from the first pressure sensor 51 that pressure in the access line 34 has risen a predetermined amount above initial operating conditions. In each case, the operator may instruct the control processor 122 via the touch panel 116 to proceed to the halt treatment step 230 or to override the advisory alarm and continue with the perform treatment step 222. If the operator elects to override the alarm, treatment continues and the alarm condition is rechecked by the monitor processor after a predetermined period of time previously stored in the monitor memory 142.

Two conditions which constitute advisory alarms can escalate to the most serious class of alarms if the conditions deteriorate. One such condition involves detection by the monitor processor 140 that the access pressure measured by the first pressure sensor 51, has fallen below the previously determined operating point. In addition to operator notification via the display 114, the control processor 122 reacts to signals from the monitor processor 140 by signalling the motor controller 128 to operate the first pump 52 at a slower rate to increase the access pressure a preset amount. A second such condition involves detection by the monitor processor 140 that return pressure, as measured by the third pressure sensor 54, has risen above the previously determined operating point. In addition to operator notification, the control processor 122 reacts to signals from the monitor processor by signalling the motor controller 128 to operate the first pump 52 at a slower rate. In either situation, the operator can elect to proceed to the flow adjust step 226 and adjust one or more flow rates, in which case the operating point will be recalculated, or proceed to the disconnect patient step 236. Alternatively, the operator can choose to override the advisory alarm and continue treatment. However, the alarm condition is not cleared until pressures return to desired levels. If, after a predetermined amount of time, the condition does not clear, the condition is treated as a most serious alarm condition, in which case the monitor processor 140 instructs the control processor 122 to cause the apparatus 30 to enter into its safe state. Thereafter, the operator can proceed to the adjust flows step 226 or to the disconnect patient step 236, or override the alarm condition in which case the monitor processor 140 rechecks the alarm after a predetermined amount of time.

In addition to detecting alarm conditions as described above, the monitor processor 140 evaluates pressure measurements in the primary circuit 38 and determines if conditions are indicative of a pinched access line 34 or return line 35, in which case the control processor 122 is directed to modify the rate of pumping of the first pump 52 below its initial rate as previously determined to achieve an initial blood flow rate until the condition is deemed corrected. If the access line 34 is pinched, a pressure decrease below a first predetermined minimum pressure is sensed by the first pressure sensor 51. If the return line 35 is pinched, a pressure increase above a first predetermined maximum pressure is sensed by the third pressure sensor 54. Upon detection of such a pressure decrease or increase, the control processor 122 is directed to decrease the pumping rate of the first pump 52 in one or more predetermined, incremental steps. After each step, pressure measurements from the first and/or third pressure sensors 51 and 54 are obtained for a predetermined period of time. If pressure measurements are constant, the monitor processor 140 directs the control processor 122 to incrementally increase the pump rate of the first pump 52 until the initial blood flow rate rate is achieved. If, however, the pressure sensed by the first sensor 51 continues to decrease or the pressure sensed by the third sensor 54 continues to increase, the control processor 122 is directed to further decrease the rate of pumping of the first pump 52. The rate of pumping of the first pump 52 is continuously decreased in this manner until a second predetermined minimum pressure is detected by the first pressure sensor 51, a second predetermined maximum pressure is detected by the third pressure sensor 54, or until a predetermined period of time has elapsed, at which point an alarm condition is indicated and an alarm emitted and displayed, as previously described.

As mentioned previously, the monitor processor 140 can evaluate the integrity of the pressure sensors 51, 53, 54 and 83 when the pressure sensors are of a conventional design having a membrane centrally located in a disposable chamber. If there is a slow leak in the air compartment, the membrane may lock in a position on either side of the middle of the disposable chamber, in which case the pressure sensor is typically unresponsive. To determine the integrity of the air chamber, the flow rate of the liquid being measured may be instantly changed at regular intervals. Simultaneously, the change in pressure is measured by the pressure sensor over a predetermined period of time is calculated (dp/dt). If the change in pressure is less than a predetermined value, malfunction of the pressure sensor is indicated, which is treated by the monitor processor 140 as an alarm condition and an alarm is emitted and/or displayed.

Presently preferred embodiments of the present invention and many of its improvements have been described with a degree of particularity. It should be understood that the present invention is defined by the spirit and scope of the following claims.

We claim:

1. A method for treating blood from a patient extracorporeally by a treatment which transfers matter to or from the blood through a semipermeable membrane, the semipermeable membrane being part of a filtration unit of an apparatus and dividing the filtration unit into a primary chamber and a secondary chamber, the primary chamber receiving the blood and the matter transferred across the semipermeable membrane into the blood, the secondary chamber receiving the matter to be transferred into the blood and the matter transferred across the semipermeable membrane from the blood, said method comprising the steps of:

establishing an extracorporeal blood flow primary circuit from the patient through the primary chamber and back to the patient;

controlling the flow of blood through the primary circuit;

selectively supplying a replacement fluid to the blood in the primary circuit prior to returning the blood to the patient;

controlling the amount of the replacement fluid supplied to the blood in the primary circuit;

establishing a secondary circuit for the flow of fluid through the secondary chamber;

selectively supplying a one of a secondary fluid containing matter which is to be transferred across the semipermeable membrane into the blood or a secondary fluid to remove matter from the secondary chamber which has been transferred across the semipermeable membrane from the blood to the secondary chamber;

controlling the amount of secondary fluid supplied to the secondary chamber;

collecting fluid exiting from the secondary chamber;

controlling the amount of fluid collected from the secondary chamber;

selecting one of a plurality of different extracorporeal blood treatments to be performed by the apparatus;

frequently determining and automatically controlling the rate of flow of fluid through the primary circuit, the rate of flow of replacement fluid into the primary circuit, the rate of flow of secondary fluid into the secondary chamber and the rate of flow of fluid collected from the secondary chamber according to the extracorporeal blood treatment selected;

storing information defining which of the ones of the replacement fluid and the secondary fluid are to be supplied and defining the flow rates in the primary and secondary circuits for each of the plurality of treatments;

providing a blood leak detector;

detecting blood in the secondary circuit with the blood leak detector; and during treatment periodically conducting self-tests of the blood leak detector to determine the operational integrity of the blood leak detector during treatment.

2. The method as defined in claim 1 further comprising the step of:

controlling the rate of fluid flow in the primary and secondary circuits in response to detecting a blood leak in the secondary circuit.

3. The method as defined in claim 1 further comprising the step of:

putting the apparatus in a safe state in response to detecting a blood leak in the secondary circuit.

4. The method as defined in claim 1, wherein the apparatus further includes a blood leak detector in the secondary circuit operative, said method further comprising the step of:

automatically detecting blood in the secondary circuit.

* * * * *